United States Patent [19]

Gasser et al.

[11] Patent Number: 5,008,303

[45] Date of Patent: Apr. 16, 1991

[54] MOLDING COMPOSITION FOR MAKING CASTING PATTERNS

[75] Inventors: Oswald Gasser, Seefeld; Rainer Guggenberger, Herrsching; Klaus Ellrich, Wörthsee, all of Fed. Rep. of Germany

[73] Assignee: ESPE Stiftung & Co. Produktions- und Vertriebs KG, Seefeld, Fed. Rep. of Germany

[21] Appl. No.: 471,087

[22] Filed: Jan. 26, 1990

[30] Foreign Application Priority Data

Jan. 27, 1989 [DE] Fed. Rep. of Germany ....... 3902417

[51] Int. Cl.$^5$ ............ B22C 7/00; B22C 9/02; C08F 2/00
[52] U.S. Cl. ...................... 522/64; 522/79; 522/80; 526/209; 526/213
[58] Field of Search ............ 522/64, 79, 80; 526/209, 213

[56] References Cited

U.S. PATENT DOCUMENTS

| | | | |
|---|---|---|---|
| 4,603,726 | 8/1986 | Pfannenstiel et al. | 164/35 |
| 4,720,319 | 1/1988 | Gasser | 522/28 |
| 4,900,777 | 2/1990 | Ball et al. | 526/213 |

FOREIGN PATENT DOCUMENTS 044244 2/1987 Japan .

*Primary Examiner*—Marion E. McCamish
*Assistant Examiner*—Susan Berman
*Attorney, Agent, or Firm*—Robert W. Becker & Associates

[57] ABSTRACT

A molding composition for making casting patterns is described containing (a) 10–99.89, preferably 20–90%, by weight of at least one di or polyfunctional acrylic acid and/or methacrylic acid ester which burns without residue, (b) 0.01–5% by weight of an initiator system which can initiate the radical polymerization and (c) 0–80, preferably 10–70%, by weight of organic fillers, pigments and other auxiliary substances burning without residue, the quantity particulars each being related to the total amount of (a)+(b)+(c), characterized in that it further contains (d) 0.1–30, preferably 1–20%, by weight with respect to the component (a) of a chemically inert organic compound burning without residue and having a boiling point and/or sublimation point in the range >150° C.

This molding composition is distinguished by not causing any faults in the casting jacket, in particular no crack formation, on burning out of the mold.

7 Claims, No Drawings

MOLDING COMPOSITION FOR MAKING CASTING PATTERNS

BACKGROUND OF THE INVENTION

The invention relates to molding compositions burning without residue for making casting patterns.

For making metallic castings, in particular in the field of dental technology, it is usual firstly to make a casting pattern from wax, to secure to the wax a prefabricated casting passage, to cover the casting pattern with a refractory embedding composition and finally to remove the wax composition by steaming out or burning the wax at temperatures between about 500° C. and 700° C. The negative mold obtained is filled with a liquid metal. After cooling and removing from the mold a casting is obtained which has the same shape as the casting pattern of wax. In analagous procedure casting molds can be made for moldings from castable glass or castable glass ceramic.

In view of the disadvantages of the wax modelling technique, which are in particular the danger of undesired deformations or damage of the patterns, the method now adopted is to make such casting patterns from plastic. After initially using so-called autopolymerizing plastics such as methyl methacrylate, recently there has been an increased tendency to use photopolymerizable plastic compositions burning without residue, cf. DE-OS 3,240,907.

One difficulty which occurs when using such photopolymerizable plastic compositions is that when burning out the molding composition cracks can easily form in the casting jacket. These cracks arise due to the pronounced thermal expansion of the molding composition in the heating process and the simultaneously counteracting thermal expansion of the casting jacket. In the casting operation the liquid metal, in particular gold, penetrates into the cracks so that metal flashes arise on the molded metal part which make finishing work necessary. Apart from the resulting additional work involved there is the disadvantage of the not inappreciable material losses.

The problem underlying the invention is to provide a molding composition burning without residue for making casting patterns for metal castings which during burning out from the mold does not cause any disturbances of the casting jackets, in particular any formation of cracks.

SUMMARY OF THE INVENTION

According to the invention, by adding certain organic compounds the expansion behavior of the molding composition in the burning out operation can be influenced so that no cracks form at the casting jacket.

The subject of the invention is a molding composition for making casting patterns containing
(a) 10-99.89, preferably 20-90%, by weight of at least one di or polyfunctional acrylic acid and/or methacrylic acid ester which burns without residue,
(b) 0.01-5% by weight of an initiator system which can initiate the radical polymerization and
(c) 0-80, preferably 10-70%, by weight of organic fillers, pigments and other auxiliary substances burning without residue,
the quantity particulars each being related to the total amount of (a)+(b)+(c), characterized in that it further contains (d) 0.1-30, preferably 1-20%, by weight with respect to the component (a) of a chemically inert organic compound burning without residue and having a boiling point and/or sublimation point in the range >150° C.

The boiling point of the organic compound preferably lies in the range from 200° to 320° C. and in particular in the range from 250° C. to 300° C.

The proportion of the organic compound used as component (d) in the molding composition is preferably 1 to 20% by weight, in particular 5 to 15% by weight, and quite particularly about 10% by weight with respect to component (a).

Organic compounds suitable as such additives are any compounds which satisfy the aforementioned conditions. The property "chemically inert" means that the compound does not enter any reactions with the organic polymerizable composition or with the other constituents of the molding composition. This property must also be retained up to the boiling/sublimation temperature of the additive.

Preferably, these additives are nonpolar or have low polarity.

Specific examples of organic compounds suitable as additives are diphenyl ( , bp 255° C.), bibenzyl (1,2-diphenylethane,

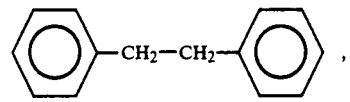, bp 284° C.) and decanol ($CH_3(CH_2)_9OH$, bp about 230° C.).

2,3,6-trimethylnaphthalene (bp 263° C.),
hexamethylbenzene (bp 264° C.),
diphenylmethane (bp 265.6° C.),
1,1-diphenylethane (bp 268° C.),
pentadecane (bp 270.5° C.),
2,3-dimethyldiphenyl (bp 273° C.),
cinnamyl alcohol (bp 275.5° C.),
dibenzyl ether (bp/decomposition point 295 to 298° C.),
hexaethylbenzene (bp 298° C.) and
phthalic acid diethyl ester (bp 298° C.).

The additives according to the invention should have a boiling point as indicated above. However, compounds having a sublimation point in said range can readily be used. Fundamentally, an additive decomposing in the temperature range specified is also suitable as long as the decomposition products do not enter reactions with the other constituents of the molding composition, thereby being held fixed in the latter. In particular, the additives according to the invention should not contain any reactive double bonds, for example polymerizable vinyl groups, or any temperature-unstable bonds such as for example peroxides forming radicals at higher temperatures.

Metal castings made using the molding compositions do not have any metal flashes and consequently no involved finishing work is required and the material losses are minimized.

The polymerizable organic compositions are preferably photopolymerizable because photopolymerizable compositions have particular advantages due to their hardenability at room temperature and their long processing time. Fundamentally, however, the invention is also applicable to autopolymerizing plastics which can be cured mostly by the principle of redox polymerization.

The photopolymerizable compositions contain the usual photoinitiators, for example benzophenones, benzoin ethers, benzil ketals, thioxanthones and aromatic or aliphatic diketones. Particularly suitable are 1,2-diketones, in particular camphor quinone.

In addition, so-called photoactivators can be used, for example organic phosphites or amines. In the case of the 1,2-diketones tertiary amines are particularly effective activators.

Also suitable as photoinitiators are mono and bisacyl phosphine oxides, such as 2,4,6-trimethylbenzoyl-diphenyl phosphine oxide and bis-(2,6-dichlorobenzoyl)-4-n-propylphenyl-phosphine oxide. However, also suitable are other compounds of this type as are described in European Pat. publications Nos. 73413, 7508, 47902, 57474 and 184095. The concentration of the photoinitiators is preferably 0.1 to 3% by weight, in particular preferably 0.1 to 2% by weight, with respect to the total mass of polymerizable compositions.

Suitable as photopolymerizable compounds are for example the esters of acrylic acid and methacrylic acid. Difunctional or polyfunctional (meth)acrylic acid esters lead to particularly deformation-stable casting patterns. For example, the long-chain monomers of U.S.-PS 3,066,112 may be advantageously used, i.e. the reaction products of bisphenol A and glycidyl methacrylate or also their derivatives obtained by addition of isocyanates. Also well suited are the diacrylic and dimethacrylic acid esters of the ethoxylated and/or propoxylated bisphenol A having 2 to 4 ethylene oxide or propylene oxide units per bisphenol A unit. Further suited are the acrylic acid and methacrylic acid esters of at least bifunctional aliphatic alcohols such as triethylene glycol-di(meth)acrylate, ethylene glycol-di-(meth)acrylate, hexanediol-di-(meth)-acrylate and also trimethylolpropane-tri-(meth)acrylate.

Also particularly suitable are the diacrylic and dimethacrylic acid esters, specified in DE-PS 2,816,823, of bishydroxymethyl-tricyclo [5.2.1.0$^{2,6}$]-decane or also the diacrylic and dimethacrylic acid esters of the compounds of bishydroxymethyl-tricyclo [5.2.1.0$^{2,6}$]-decane lengthened with 1-6 ethylene oxide and/or propylene oxide units. Also well suited are the methacrylic acid esters described in European publication No. 235826, for example triglycol acid-bis-[3(4)-methacrylic oxymethyl-8(9)-tricyclo [5.2.1.0$^{2,6}$]-decylmethyl esters].

For setting the desired viscosity it may also be expedient to use mixtures of monomers and/or unsaturated polymers made therefrom. In addition to the at least bifunctional acrylic acid and methacrylic acid esters up to 90% by weight with respect to the polymerizable constituents, preferably up to 50% by weight, monofunctional methacrylic acid esters may be used, for example methyl mechacrylate.

The polymerizable compounds are preferably up to at least 10% by weight bifunctional or polyfunctional acrylic acid and/or methacrylic acid esters, particularly preferably up to at least 20, very particularly preferably up to at least 50% by weight. In a preferred embodiment as polymerizable compounds only bifunctional or polyfunctional acrylic acid and methacrylic acid esters are used.

Mixtures of polythiols and polyallyl compounds in stoichiometric ratio corresponding to U.S.-PS 3,898,349 may also be employed as photopolymerizable compounds.

To increase the mechanical strength, reduce the polymerization shrinkage and to control the viscosity, the molding compositions may also contain suitable fillers and/or soluble organic plastics. Suitable for example are polymethyl methacrylate, nylon pearls, polyvinyl acetate, polyvinyl fluoride or polystyrene. It must however be ensured that the selected additives burn without residue. The precipitation polymers according to EP-A-0 235 825 have proved to be particularly advantageous. However, it is also possible to use organic fillers obtained by polymerization of polymerizable compounds, as are also employed in the preparation according to the invention. This means that a prepolymer is made from said compounds and ground down so that the grain distribution has a mean grain size of 1 to 15 $\mu$m, preferably 1 to 10 $\mu$m, particularly preferably 1 to 5 $\mu$m. It should be ensured that no organic abrasion which might impair the burning without residue adheres to the ground polymer.

The viscosity of the preparation according to the invention is set in a favorable manner by the steps mentioned so that the compound can be applied thinly with a brush or spatula but only has a low flowability without the action of shearing forces.

For setting the flow behavior and the adhesive properties of the preparation according to the invention plasticizers and emulsifiers may be added to the composition, for example the stearyl, oleyl and glycerol esters of polyoxyethylene, polyalkylene glycol ethers, polyoxyethylene aryl ethers and the polyoxyethylene sorbitan monoesters of lauric acid, palmitic acid and oleyl and stearic acid. Also suitable are the copolymers of ethylene oxide and propylene oxide with molecular weights between 500 and 5000, preferably between 1000 and 4000. As plasticizers it is also possible to use citrates, such as tributyl citrate, phthalic acid esters of long-chain alcohols, such as dioctyl or dinonyl phthalate, and also completely nonpolar compounds such as thinly liquid paraffin oils or dibenzyl toluene.

For better distinction from the jaw model and for checking the applied layer thickness it is advantageous to provide the photopolymerizable composition used with pigments and/or opacifying agents.

The wavelength of the light used in the photopolymerization must be chosen so that it corresponds to the effective light absorption of the photoinitiator. Because of the harmlessness of the radiation and the simple and economic construction of the irradiating unit it is advantageous to use visible light in the wavelength range from about 400 to 500 nm, preferably together with 1,2-diketone initiators and/or acyl phosphine oxides.

The compositions, which may further contain the usual stabilizers and inhibitors, are kept ready for use in light-tight containers.

The compositions according to the invention are suitable for making any castings, in particular in the field of dental technology. Another field of use is however orthopedic prosthetics, for example in castings for filling bone defects, or the field of jewelry technology. Examples of metal castings in the field of dental technology are inlays, crowns, bridges, secondary parts of cone crowns, male die parts attachments, telescopic anchors, web caps and the like. Castings of glass ceramic may be used in particular in the form of inlays, onlays, crowns and veneer shells.

The composition or compound according to the invention is particularly suitable for laminate application, (cf. DE-OS 3,240,907), advantageously layers each of about 0.5 mm to 1 mm thickness being applied and the composition then cured by irradiating with a light source. This permits a particularly careful and economic working without large losses of material. The application in thin layers substantially compensates the polymerization shrinkage. After the application of the first layer of the material according to the invention the further operations may be carried out also with conventional materials such as wax if this does not impair the stability of the overall component. After completion of the casting model or pattern by irradiating the photopolymerizable preparation, in the usual manner a casting passage is attached and the casting pattern embedded in a casting jacket by means of a potting compound. The casting jacket is thereafter preferably heated for a predetermined period of time (preferably 30 to 60 minutes) to a temperature in the range of the boiling point of the additive used according to the invention. Thereafter the actual burning-out operation is carried out. The temperature therein is preferably increased to 550 to 600° C. After a certain holding time of for example 10–20 minutes further heating is contained up to the final temperature in the region of 700° C. This final temperature is retained for about 30 to 60 minutes. Thereafter, the negative mold in the casting jacket is preferably filled in a casting centrifuge with a noble metal alloy. After cooling to room temperature the cast molding can be removed from the embedding and possibly worked out. As already mentioned, the finishing work for removing casting flashes is not necessary.

Hereinafter the invention will be explained in detail with the aid of examples.

EXAMPLE 1

80% by weight urethane methacrylate (Plex 666100, Röhm Company) is stirred with slight heating with 19.5 parts by weight triethylene glycol dimethacrylate and 0.5 parts by weight bis-(2,6-dichlorobenzoyl)-4-n-propylphenyl phosphine oxide until a homogeneous clear solution is obtained. The percentages by weight of additive according to the invention indicated in the table are added to this solution. Thereafter, the viscous solutions are cast into a brass mold the internal dimensions 40×5×1 mm and exposed by means of a dental halogen lamp (Elipar, ESPE Company) for 1 minute until complete polymerization. The specimens were then removed from the mold and after storing for 30 minutes at room temperature provided with a casting passage of wax and embedded in a casting jacket by means of potting compound (Deguvest, Degussa Company, set to 50% of the maximum expansion). Thereafter the casting jacket (size 3) is heated in a conventional preheating oven (Combilabor CL-VS 2002 Heraeus) to 230° C. This temperature is retained for 30 minutes and thereafter heating continued up to 580° C. After 15 minutes holding time heating is continued up to 700° C. final temperature which is retained for a further 45 minutes. Thereafter, the casting jackets are introduced into a conventional casting centrifuge (Formax 35 K, Bego) and the negative mold filled with noble metal alloy (Hera SG, Heraeus). After cooling to room temperature the cast molding can be removed and worked out if necessary.

As apparent from Table 1 the molding, which does not contain any additive according to the invention in the modeling plastic, led to pronounced crack formation in the casting jacket manifesting itself in casting and tear-off flashes in the molding (casting). In addition the working out is very involved and large losses of noble metal alloy are not to be avoided. If the modeling plastic contains the additives according to the invention the casting jacket remains stable, the molding does not exhibit any casting flashes and the working out is restricted to removal of the potting material.

TABLE 1

| % Additive | Boiling or sublimation point of the additive | | Assessment of the cast object |
| --- | --- | --- | --- |
| A (comparison) | 0 | — | cracks in the casting jacket - flashes on the cast object |
| B (according to the invention) | 9% by weight diphenyl | 255° C. | no cracks no casting flashes |
| C (according to the invention) | 10% by weight dibenzyl | 285° C. | no cracks no casting flashes |
| D (according to the invention) | 9% by weight decanol | about 230° C. | no cracks no casting flashes |

EXAMPLE

Modeling Paste 90 parts by weight of a methacrylic ester mixture according to Example 1 of EP 0 235 826, 60 parts by weight bis(acryloxymethyl)-tricyclo[5.2.1.0.$^{2,6}$]-decane, 15 parts by weight dibenzyl and 0.53 parts by weight bis-(2,6- dichlorobenzoyl)-4-n-propylphenyl phosphine oxide are stirred with slight heating until a homogeneous clear solution is obtained. 7.5 parts by weight of a copolymer of ethylene and propylene oxide and 25.5 parts by weight of an organic filler according to Example 1 of EP-A 0 270 915 are added to this solution and kneading continued until a homogeneous supple paste is formed. The modeling paste thus obtained can be excellently worked to patterns and has the following physical measured values. Polymerizable layer thickness (20 seconds exposure with a dental radiator, Elipar, ESPE Company ) 7.4 mm, viscosity 6.3 Pa.s, surface hardness 71 MPa, compressive strength 300 MPa, flexural strength 70 MPa. If a specimen as described in Example 1 is made from the modeling material according to this example and filled with noble metal, the casting has a perfectly smooth surface (i.e. no burning residue whatever) and exhibits no casting flashes at all at the corners and edges of the casting.

EXAMPLE 3

Making the Secondary Part of a Cone Crown

For making a cone crown on the outer surface of a primary crown finish milled in metal a uniform layer of about 0.5 mm of the photohardening material is formed by laminate application of the modeling paste in accordance with Example 2 and exposure in each case. After the irradiation the plastic cap can be removed from the primary crown for checking the inner side. After the check the resulting exactly fitting sleeve is again placed onto the primary member and the anatomical form of the secondary member brought up by modeling with further portionwise application and subsequent hardening of the photohardening plastic. The secondary crown thus obtained is then removed from the primary crown and provided in the usual manner with a casting pin of wax and surrounded with refractory potting or embedding material (Deguvest HFG, Degussa). The photocuring plastic is burned without residue by a heating operation as described in Example 1. Thereafter the casting and removing from the embedding with the necessary working out can be effected. The working out can easily be done by simple sand blasting (e.g. with bright blasting beads). There is no need to remove any casting flashes and surface roughness of the crown by complicated working out. The secondary crown obtained in metal is identical in shape and accuracy to the secondary crown of photocuring material and thus has a good cone adhesion to the primary crown. In similar manner the secondary members of telescopic crowns and attachments may be made, including the lock elements (e.g. rotational, swing or stretch bolts).

The present invention is, of course, in no way restricted to the specific disclosure of the specification and examples, but also encompasses any modifications within the scope of the appended claims.

What we claim is:

1. A molding composition, for making casting patterns, comprising:
   (a) 10-99.89% by weight of at least one of the group consisting of di and polyfunctional acrylic acid and methacrylic acid ester, all of which burn without leaving a residue;
   (b) 0.01-5% by weight of an initiator system that can initiate the radical polymerization;
   (c) 0-80% by weight of at least one of the group consisting of organic fillers, pigments, and other auxiliary substances, all of which burn without leaving a residue, whereby the quantity particulars of the respective components of (a), (b), and (c) are each related to the total amount of (a)+(b)+(c); and
   (d) 0.1-30% by weight, with respect to component (a), of a chemically inert organic compound that burns without leaving a residue and has a boiling point and/or sublimation point in the range of >150° C.

2. A molding composition according to claim 1, which includes 20-90% by weight of component (a), 10-70% by weight of component (c), and 1-20% by weight, with respect to component (a), of component (d).

3. A molding composition according to claim 1, in which component (d) has a boiling point and/or sublimation point in the range of from 200 to 320° C.

4. A molding composition according to claim 3, in which component (d) has a boiling point and/or sublimation point in the range of from 250-300° C.

5. A molding composition according to claim 1, which includes 5-15% by weight, with respect to component (a), of component (d).

6. A molding composition according to claim 1, in which component (d) is nonpolar or has a low polarity.

7. A molding composition according to claim 1, which contains a photoinitiator.

* * * * *